(12) United States Patent
Inui et al.

(10) Patent No.: US 8,329,973 B2
(45) Date of Patent: Dec. 11, 2012

(54) MULTIPLE ZEOLITE CATALYST

(75) Inventors: Tomoyuki Inui, Kizugawa (JP); Masayuki Inui, legal representative, Kizugawa (JP); Mohammad A. Ali, Dhahran (SA); Muhammad A. Al-Saleh, Dhahran (SA); Syed A. Ali, Dhahran (SA); Khalid Al-Nawad, Dhahran (SA); Tsutomo Okamoto, Higashikurume (JP); Katsuhiko Ishikawa, Yokohama (JP); Minoru Hatayama, Yokohama (JP)

(73) Assignees: King Fahd University of Petroleum and Minerals, Dhahran (SA); Japan Cooperation Center, Petroleum (JCCP), Tokyo (JP)

( * ) Notice: Subject to any disclaimer, the term of this patent is extended or adjusted under 35 U.S.C. 154(b) by 0 days.

(21) Appl. No.: 13/353,085

(22) Filed: Jan. 18, 2012

(65) Prior Publication Data

US 2012/0116139 A1    May 10, 2012

Related U.S. Application Data

(63) Continuation of application No. 12/219,927, filed on Jul. 30, 2008, now abandoned.

(51) Int. Cl.
*C07C 6/12* (2006.01)
(52) U.S. Cl. ...................................................... 585/475
(58) Field of Classification Search .................. 585/475
See application file for complete search history.

(56) References Cited

U.S. PATENT DOCUMENTS

| | | | |
|---|---|---|---|
| 3,894,934 A | 7/1975 | Owen et al. |
| 3,928,174 A | 12/1975 | Bonacci et al. |
| 4,116,814 A | 9/1978 | Zahner |
| 4,992,402 A | 2/1991 | Schweizer |
| 5,773,676 A | 6/1998 | Drake et al. |

(Continued)

FOREIGN PATENT DOCUMENTS

EP    55529    1/2003

(Continued)

OTHER PUBLICATIONS

Huheey et al., *Inorganic Chemistry*, 4th ed., Harper Collins College Publishers, New York, 1993, pp. 745-748.

(Continued)

*Primary Examiner* — Thuan D Dang
(74) *Attorney, Agent, or Firm* — Richard C. Litman

(57) ABSTRACT

The multiple zeolite catalyst is a catalytic composition used to convert $C_{9+}$ alkylaromatic hydrocarbons to BTX, particularly commercially valuable xylenes. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VIB and Group VIII of the Periodic Table of the Elements. The two zeolites should have different physical and chemical characteristics, such as pore size and acidity. An exemplary catalyst includes mordenite, ZSM-5, and 3 wt. % molybdenum. The transalkylation reaction may be conducted in one or more reactors with a fixed bed, moving bed, or radial flow reactor at 200-540° C., a pressure of 1.0-5.0 MPa, and liquid hourly space velocity of 1.0-5.0 per hour.

8 Claims, 1 Drawing Sheet

U.S. PATENT DOCUMENTS

| | | | |
|---|---|---|---|
| 5,847,256 | A | 12/1998 | Ichioka et al. |
| 5,866,744 | A | 2/1999 | Wu et al. |
| 5,905,051 | A | 5/1999 | Wu et al. |
| 5,942,651 | A | 8/1999 | Beech, Jr. et al. |
| 6,037,294 | A | 3/2000 | Drake et al. |
| 6,040,259 | A | 3/2000 | Mohr et al. |
| 6,300,270 | B1 | 10/2001 | Wu et al. |
| 6,417,421 | B1 | 7/2002 | Yao |
| 6,504,073 | B1 | 1/2003 | Ushio et al. |
| 6,514,896 | B1 | 2/2003 | Drake et al. |
| 6,855,854 | B1 | 2/2005 | James, Jr. |
| 6,972,348 | B2 | 12/2005 | Negiz et al. |
| 7,148,391 | B1 | 12/2006 | Buchanan et al. |
| 2001/0014645 | A1 | 8/2001 | Ishikawa et al. |
| 2002/0091293 | A1 | 7/2002 | Chang et al. |
| 2003/0036670 | A1* | 2/2003 | Oh et al. .................. 585/400 |
| 2003/0092950 | A1 | 5/2003 | Xiao et al. |
| 2005/0197518 | A1 | 9/2005 | Miller et al. |
| 2005/0234279 | A1 | 10/2005 | Serra et al. |
| 2006/0100471 | A1 | 5/2006 | Serra Alfaro et al. |
| 2006/0128555 | A1 | 6/2006 | Shan et al. |

FOREIGN PATENT DOCUMENTS

| | | |
|---|---|---|
| JP | 62-71546 | 4/1987 |
| JP | 09-038505 | 2/1997 |
| JP | 09-155198 | 6/1997 |

OTHER PUBLICATIONS

Sherman, J.D., "Synthetic zeolites and other microporous oxide molecular sieves," Proc. Natl. Acad. Sci. USA, vol. 96, (Mar. 1999) pp. 3471-3478 (p. 3471 only).

* cited by examiner

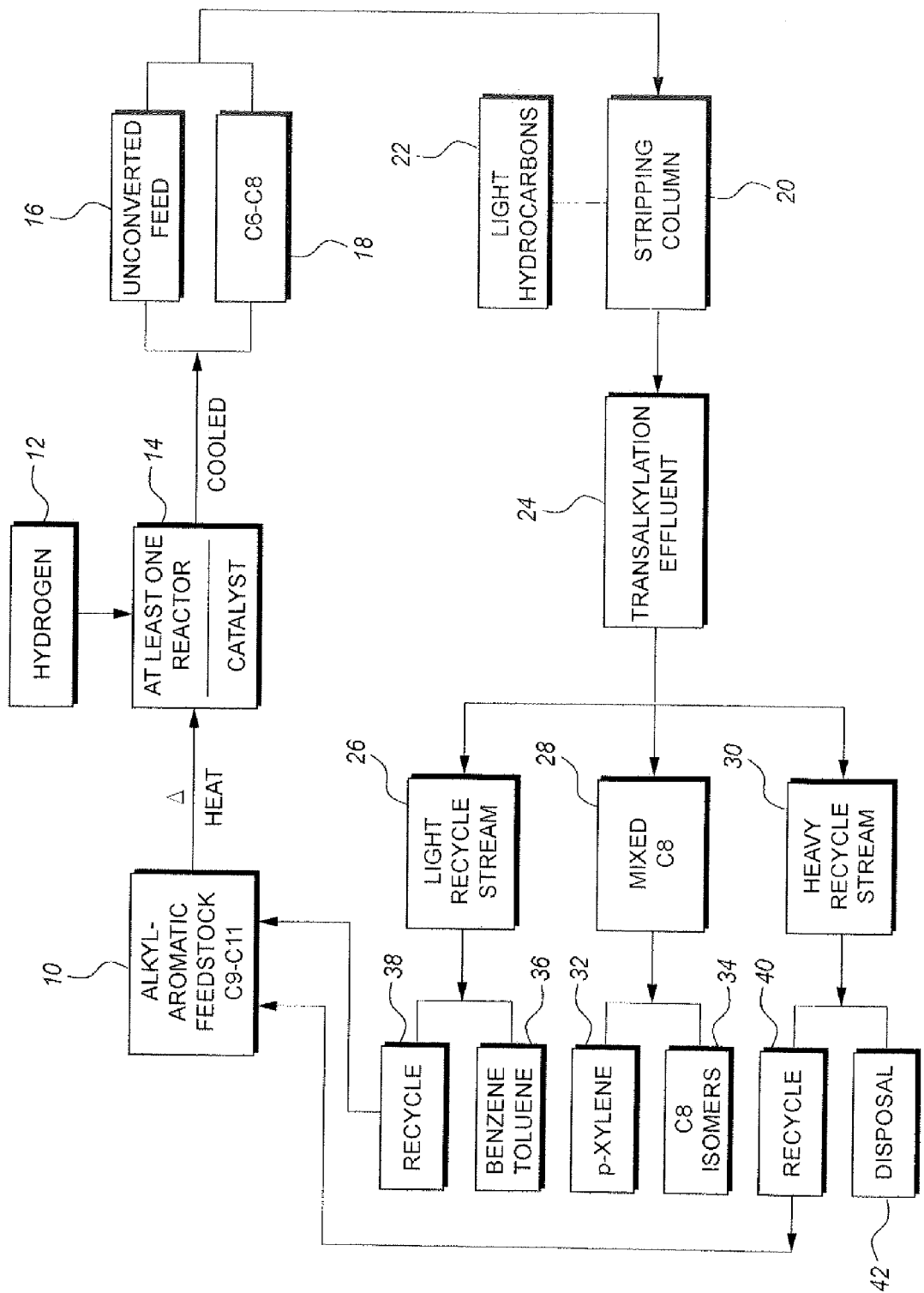

US 8,329,973 B2

MULTIPLE ZEOLITE CATALYST

CROSS REFERENCE TO RELATED APPLICATION

This application is a continuation of application Ser. No. 12/219,927, filed Jul. 30, 2008, now abandoned.

BACKGROUND OF THE INVENTION

1. Field of the Invention

The present invention relates to catalysts used in petroleum refining, and particularly to a multiple zeolite catalyst used to convert heavy aromatic hydrocarbons, principally $C_{9+}$ aromatics, to BTX (benzene, toluene, and xylene), and particularly to commercially valuable xylene isomers.

2. Description of the Related Art

Aromatic hydrocarbons are the building blocks for many industrially important products. They are generally produced in a petrochemical complex. There are several commercial processes producing aromatics especially xylenes isomers, using a variety of reactions. Xylene isomers, para-xylene, meta-xylene and ortho-xylene, are important intermediates, which find wide and varied application in chemical syntheses. Upon oxidation, p-xylene yields terephthalic acid, which is used in the manufacture of polyester plastics and synthetic textile fibers (such as Dacron), films (such as Mylar), and resins (such as polyethylene terephthalate, used in making plastic bottles). m-Xylene is used in the manufacture of plasticizers, azo dyes, wood preservers, etc. o-Xylene is feedstock for phthalic anhydride production, which is used to make polyester, alkyd resins, and PVC plasticizers.

Xylene isomer streams from catalytic reforming or other sources generally do not match demand proportions as chemical intermediates. p-Xylene, in particular, is a major chemical intermediate with rapidly growing demand, but amounts to only 20 to 25% of a typical $C_8$ aromatics stream. Among the aromatic hydrocarbons, the overall importance of the xylenes rivals that of benzene as a feedstock for industrial chemicals. The xylenes are produced from petroleum by the reforming of naphtha in insufficient volume that is difficult to meet the demand, and conversion of other hydrocarbons is necessary to increase the yield of xylenes.

A current objective of many aromatics production facilities is to increase the yield of xylenes by converting heavy aromatics, such as $C_9$, $C_{10}$ and $C_{11+}$, and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene, thus, is a favorable objective, and processes to convert $C_{9+}$ aromatics have been commercialized to obtain high xylene yields.

Aromatic hydrocarbon compounds contained in a gasoline base generally have higher octane values and are superior as a gasoline base because of their high calorific value. Among them, toluene and aromatic hydrocarbon compounds, those having eight carbon atoms especially, have higher octane values and driveability levels; thus, it is desirable to increase the volume of $C_8$ aromatic compounds in gasoline. In particular, methods of directly converting aromatic hydrocarbon compounds having nine or more carbon atoms in a gasoline fraction into toluene and aromatic hydrocarbon compounds having eight carbon atoms are significantly meaningful.

Reactions of aromatic hydrocarbon compounds to convert aromatic hydrocarbon compounds to compounds having a different number of carbon atoms include the transalkylation reaction and the disproportionation reaction. A transalkylation reaction is one in which an alkyl group, e.g., a methyl group, is detached from a first compound and then attached to a second compound. A disproportionation reaction is a reaction in which a single compound acts as both an oxidizing agent and a reducing agent.

A well known process regarding these reactions is the manufacture of xylenes utilizing the disproportionation reaction of toluene, i.e., two molecules of toluene react to form one molecule of benzene and one molecule of xylene (by transfer of a methyl group from one molecule of toluene to the other, a transalkylation reaction). Transalkylation reactions, however, are not limited to the disproportionation of toluene. Other methods of increasing xylene yields operate through inducing transalkylation by adding aromatic hydrocarbon compounds having nine or more carbon atoms into the starting materials, resulting in such reactions as the addition of one mole of toluene to one mole of a $C_9$ aromatic hydrocarbon to produce two moles of xylene. Examples of such transalkylation reactions are illustrated in paragraphs [0009] through [0011] of U.S. Patent Publication 2005/0187518, which are hereby incorporated by reference.

Further, it is known to separate isomers through molecular sieves formed by zeolites. Zeolites are generally hydrated aluminum and calcium (or sodium) silicates that can be made or selected with a controlled porosity for catalytic cracking in petroleum refineries, and may be natural or synthetic. The pores may form sites for catalytic reactions to occur, and may also form channels that are selective for the passage of certain isomers to the exclusion of others. Zeolites may serve as Brönsted acids by hydrogen ion exchange by washing with acids, or as Lewis acids by heating to eliminate water from the Brönsted sites. For example, the zeolite ZSM-5 $(Na_3Al_3Si_{93}O_{192} \cdot 16H_2O)$ has a pore size that results in the formation of channels of such size and shape that it forms a selective sieve for xylene isomers. The alkylation of toluene by methanol will form a mixture of all three xylene isomers. p-Xylene will pass through the channels in ZSM-5 due to its linear configuration, while o-xylene and m-xylene will not pass through the pores, although they may subsequently rearrange to p-xylene under the acidic conditions in the pores and then pass through the sieve. See Huheey et al., *Inorganic chemistry*, 4th ed., pp. 745-748.

The catalytic activity of zeolites can also be increased by addition of a metal catalyst that activates hydrogen by breaking up molecular hydrogen to atomic hydrogen on the surface of the metal for forming intermediates in transalkylation reactions.

Many types of supports and elements have been disclosed for use as catalysts in processes to convert heavier aromatics into xylenes. However, as the number of such supports and elements attests, none have been found entirely satisfactory. Hence, an improvement of even a few percentage points in conversion efficiency may be significant, particularly when practiced at high volumes on an industrial scale in oil refining facilities. Thus, a multiple zeolite catalyst solving the aforementioned problems is desired.

SUMMARY OF THE INVENTION

The multiple zeolite catalyst is a catalytic composition used to convert $C_{9+}$ alkylaromatic hydrocarbons to BTX, particularly commercially valuable xylenes. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VIB and Group VIII of the Periodic Table of the Elements. The two zeolites should have different physical and chemical characteristics, such as pore size and acidity. An exemplary catalyst includes mordenite, ZSM-5, and 3 wt. % molybdenum. The transalkylation reaction may be conducted in one or more reactors with a fixed bed, moving bed, or radial flow reactor at 200-540° C., a pressure of 1.0-5.0 MPa, and liquid hourly space velocity of 1.0-5.0 per hour.

These and other features of the present invention will become readily apparent upon further review of the following specification and drawings.

BRIEF DESCRIPTION OF THE DRAWINGS

The sole FIGURE is a block diagram showing a process for using a multiple zeolite catalyst according to the present invention for converting $C_{9+}$ alkylaromatic feedstock into BTX.

DETAILED DESCRIPTION OF THE PREFERRED EMBODIMENTS

The present invention is a multiple zeolite catalyst used to convert $C_{9+}$ alkylaromatic hydrocarbons to BTX, particularly commercially valuable xylenes. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VIB and Group VIII of the Periodic Table of the Elements. The two zeolites should have different physical and chemical characteristics, such as pore size and acidity. An exemplary catalyst includes mordenite, ZSM-5, and 3 wt % molybdenum. The transalkylation reaction may be conducted in one or more reactors with a fixed bed, moving bed, or radial flow reactor at 200-540° C., a pressure of 1.0-5.0 MPa, and liquid hourly space velocity of 1.0-5.0 per hour.

The feed stream to the conversion process generally comprises alkylaromatic hydrocarbons in the carbon number range $C_9$ to $C_{11+}$ that may include, for example, such hydrocarbons as propylbenzenes, ethylmethylbenzenes, tetramethylbenzenes, ethyldimethylbenzenes, diethylbenzenes, methylpropylbenzenes, triethylbenzenes, and mixtures thereof.

Referring to the sole drawing, the heavy aromatics feed stream 10, characterized by $C_{9+}$ aromatics, permits effective transalkylation of light aromatics such as benzene and toluene with the heavier $C_{9+}$ aromatics to yield additional $C_8$ aromatics that are preferably xylenes. The heavy aromatics stream 10 preferably comprises at least about 95 wt. % total aromatics, and may be derived from the same or different known refinery and petrochemical processes, and may be recycled from the separation of the product from transalkylation.

The feed stream is preferably transalkylated in the vapor phase and in the presence of hydrogen. The hydrogen 12 is associated with the feed stream 10 and recycled hydrocarbons in an amount from about 0.1 moles hydrogen per mole of alkylaromatics up to ten moles per mole of alkylaromatics. This ratio of hydrogen to alkylaromatics is also referred to as the hydrogen-to-hydrocarbon ratio. The transalkylation reaction preferably yields a product having mixed xylene content, and also comprises toluene and benzene.

The feed to a transalkylation reaction zone usually is heated, first by indirect heat exchange against the effluent of the reaction zone, and then is heated to reaction temperature. The feed then is passed through a reaction zone, which may comprise one or more individual reactors 14. The use of a single reaction vessel having a fixed cylindrical bed of catalyst is preferred, but other reaction configurations utilizing moving beds of catalyst or radial-flow reactors may be employed, if desired. Passage of the combined feed through the reaction zone results in the production of an effluent stream comprising unconverted feed 16 and product hydrocarbons 18. This effluent is normally cooled by indirect heat exchange against the stream entering the reaction zone and then further cooled through the use of air or cooling water. The effluent may be passed into a stripping column 20 in which substantially all $C_5$ and lighter hydrocarbons present in the effluent are concentrated into an overhead stream 22 and removed from the process. An aromatics-rich stream is recovered as net stripper bottom, which is referred to herein as the transalkylation effluent 24.

To produce the transalkylation reaction, the process incorporates a transalkylation catalyst in at least one zone, but no limitation is intended in regard to a specific catalyst, other than such catalyst must possess a solid-acid component and a metal component. The heavier aromatic compounds will readily undergo conversion into lighter aromatics, such as toluene and xylenes. The conditions employed in the transalkylation zone normally include a temperature of from about 200° to about 540° C. The transalkylation zone is operated at moderately elevated pressures, broadly ranging from about 1.0 MPa to about 5.0 MPa. The transalkylation reaction can be effected over a wide range of space velocities. Liquid hourly space velocity (LHSV) is in the range of from about 1.0 to about 5.0 $hr^{-1}$.

The transalkylation effluent is separated into a light recycle stream 26, a mixed $C_8$ aromatics product 28, and a heavy recycle stream 30. The mixed $C_8$ aromatics product can be sent for recovery of p-xylene 32 and other valuable isomers 34. The light recycle stream may be diverted to other uses, such as to benzene and toluene recovery 36, but alternatively is recycled partially to the transalkylation zone. The heavy recycle stream 30 contains substantially all of the $C_9$ and heavier aromatics and may be partially or totally recycled 40 to the transalkylation reaction zone, or removed from the process for disposal 42 or other processing.

One type of transalkylation catalyst that may be used is based on solid-acid materials combined with a metal component. Suitable solid-acid materials include all forms and types of mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and silica-alumina or ion-exchanged versions of such solid acids. The amount of this first zeolite may range from 10 to 90 wt % of the total catalyst amount in the final dried and calcined form.

The other zeolite incorporated in the catalyst recipe is different from the first zeolite in physical and chemical characteristics, has higher acidity, and is a zeolite that is also selected from the group including mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41. The preferred amount of this second zeolite may range from 10 to 90 wt % of the total catalyst amount in the final dried and calcined form.

A refractory binder or matrix is optionally utilized to facilitate fabrication of the catalyst, to provide strength, and to reduce fabrication costs. The binder should be uniform in composition and relatively refractory to the conditions used in the process. Suitable binders include inorganic oxides, such as one or more of alumina, magnesia, zirconia, chromia, titania, boric, phosphate, zinc oxide and silica. Alumina is a preferred binder. The two different zeolites are mixed with the alumina binder in dry powdered form to yield a homogeneous mixture, thus to ensure homogeneous composition of the extrudates formed.

The multiple zeolite catalyst contains at least one metal component. One preferred metal component is a Group VIB metal, preferably molybdenum metal, although chromium or tungsten may be used in lieu of, or in addition to, molybdenum. Other preferred metal components are Group VIII metals, especially nickel, platinum and palladium. The metal component may exist within the final catalytic composite as a compound, such as an oxide, sulfide, or halide, in chemical combination with one or more of the other ingredients of the composite, or, preferably, as an elemental metal. The metal component may be present in the final catalyst composite in any amount that is catalytically effective, generally comprising about 0.01 to about 5 wt % of the final catalyst calculated on an elemental basis. The metal component may be incorporated into the catalyst in any suitable manner, such as co-precipitation or co-gelation with the carrier material, ion exchange or impregnation. Impregnation using water-soluble compounds of the metal is preferred.

EXAMPLE

For comparison purposes, an exemplary multiple zeolite catalyst according to the present invention, designated as Catalyst C, was tested against two reference catalysts, designated Catalyst A and Catalyst B. Both Catalyst A and Catalyst B have a single zeolite component. Catalyst A has two metal components and Catalyst B has a single metal component. Catalyst C has two zeolite components and a single metal component. It will be understood that the composition of Catalyst C is an exemplary embodiment only, not intended to limit the general description of the multiple zeolite catalyst of the present invention provided above.

Preparation of Catalyst A

Alumina binder (Cataloid AP-3, obtained from CCIC, Japan) in dry powder form was dispersed in deionized water to prepare a homogenously dispersed alumina. Uncalcined and untreated USY zeolite (HSZ-370HUA obtained from Tosoh Chemicals, Japan) in powder form was added to the slurry of alumina in water. The percentage of USY in the extrudates was 66%. The total mixture was thoroughly mixed into a homogeneous paste that was passed through a process of kneading, thus resulting in a thick kneaded material having enough water content to produce stable and strong extrudates. The kneaded material was extruded using a 1.5 mm diameter sieve connected a steel cylinder and piston assembly. Suitable pressure was applied during the extrusion process. The extrudates were dried and calcined. The extrudates were tested for wettability to determine the amount of water to wet the extrudates.

A solution of 0.84 g of hexammonium heptamolybdate tetrahydrate in a prescribed amount of deionized water was loaded on the extrudates to achieve 3 wt % Mo. The extrudates were dried at room temperature overnight, then dried in air circulated oven at 120° C., and then calcined in a furnace kept at 500° C. A solution of cerium nitrate in deionized water was loaded to provide 3% cerium on the extrudates. The solution was applied dropwise onto the extrudates, which were spread in a glass dish to ensure that all the extrudates were wetted with the cerium solution. The extrudates were dried at room temperature overnight, then dried in an air circulated oven at 120° C., and then calcined at in a furnace kept at 500° C.

Preparation of Catalyst B

Alumina binder (Cataloid AP-3, obtained from CCIC, Japan) in dry powder form was dispersed in deionized water for 30 minutes at room temperature to prepare a homogenously dispersed alumina. Uncalcined and untreated Mordenite zeolite (HSZ-690HOA, obtained from Tosoh Chemicals, Japan) in powder form was added to the slurry of alumina in water. The total mixture was thoroughly mixed into a homogeneous paste that was passed through a process of kneading, thus resulting into a thick kneaded material having enough water content to produce stable and strong extrudates. The kneaded material was converted into extrudates using a 1.5 mm diameter sieve connected a steel cylinder and piston assembly. Suitable pressure was applied during the extrudate formation process. The extrudates were dried and calcined. The percentage of mordenite in the extrudates was 66%.

A solution of 0.84 g of hexaammonium heptamolybdate tetrahydrate was prepared in a prescribed amount of deionized water, enough to wet the extrudates. The solution was applied dropwise on the extrudates, which were spread in a glass dish to ensure that all the extrudates were wetted with the Mo solution and to achieve 3% Mo on the extrudates. The extrudates were dried at room temperature overnight, then dried in an air circulated oven at 120° C., and then calcined in a furnace kept at 500° C.

Preparation of Catalyst C

Alumina binder (Cataloid AP-3, obtained from CCIC, Japan) in dry powder form was dispersed in deionized water to prepare a homogenously dispersed alumina. Uncalcined and untreated Mordenite zeolite (HSZ-690HOA Tosoh) having a silica to alumina ratio of 240, was added in powder form to the slurry of alumina in water, and then uncalcined and untreated ZSM-5 (CT-405, obtained from CATAL, UK) having a silica to alumina ratio of 30 was added in powder form to the slurry. In the extrudates, ZSM-5 content was less than 25%. Then, the total mixture was thoroughly mixed into a homogeneous paste that was passed through a process of kneading, thus resulting into a thick, kneaded material having enough water content to produce stable and strong extrudates. The kneaded material was converted into extrudates using 1.5 mm diameter sieve connected to a steel cylinder and piston assembly. Suitable pressure was applied during the extrusion process. The extrudates were dried and calcined.

Based on the wettability test, a solution of 0.84 g of hexaammonium heptamolybdate tetrahydrate was prepared in 12 g of deionized water. The solution was applied dropwise on the extrudates, which were spread in a glass dish, to ensure that all the extrudates were impregnated with the Mo solution. The extrudates were dried at room temperature overnight, then dried in air-circulated oven at 120° C., and then calcined in a furnace kept at 500° C.

Experimental Procedure

The catalysts were tested for transalkylation reaction in a pilot plant using a $C_{9+}$ heavy aromatics feed to demonstrate effectiveness of the catalysts for conversion and selectivity to xylenes. Table I provides the feed composition, which shows that 96.2 wt % of the feed contains different isomers of the $C_9$ aromatic components, and remaining are $C_{10}$ and $C_{11}$ components. The catalytic test consisted of loading a vertical reactor with catalyst and contacting the feed at 1.0 to 3.0 MPa under a reaction temperature of 300° C. to 500° C., at a space velocity (LHSV) of 1.0 to 5.0 hr$^{-1}$ and hydrogen to hydrocarbon ratio (H$_2$/HC) of 1 to 4. Before contacting the catalyst with the feed, the catalyst was reduced under pressurized hydrogen gas at 400° C. Various feed conversion levels were obtained at different temperatures and different space velocities and the results show high and moderate conversion of C$_9$+ feed. The data showed extremely high conversion of all aromatic components that led to the formation of especially mixed xylenes and toluene.

Total percent C$_9$+ conversion was calculated using the following equations:

Total % conversion =
$$\frac{(C_9 + \text{wt \% in the feed}) - (C_9 + \text{wt \% in the product})}{(C_9 + \text{wt \% in the feed})} \times 100$$

Selectivity,
$$\% = \frac{\text{Total wt \% xylenes produced}}{(C_9 + \text{wt \% in the feed}) - (C_9 + \text{wt \% in the product})} \times 100$$

TABLE I

C$_{9+}$ Aromatic Feed Composition

| Component | Amount (wt %) |
|---|---|
| 1,2,4-trimethyl cyclohexane | 0.2 |
| Isopropyl benzene | 1.8 |
| n-Propyl-benzene | 4.4 |
| 1-Methyl, 3-ethyl benzene | 18.5 |
| 1-Methyl, 4-ethyl benzene | 9.1 |
| 1,3,5-tri-methyl benzene | 10.1 |
| 1-Methyl, 2-ethyl benzene | 6.5 |
| 1,2,4-trimethyl benzene | 39.1 |
| 1,2,3-trimethyl benzene | 6.6 |
| Total C$_9$ Components | 96.1 |
| Total C$_{10}$+ Components | 3.9 |
| Total Components | 100 |

Results

Table II shows a comparison of the percentage conversion of C$_{9+}$ components obtained using Catalysts A, B, and C at high severity reaction conditions (400° C. and 1.5 LHSV), Catalyst C shows higher percent conversion of individual components present in the feed, especially C$_9$ components.

TABLE II

Percent Conversion at 400 C. and 1.5 LHSV

| High C$_{9+}$ % Conversion Components | Catalyst A | Catalyst B | Catalyst C |
|---|---|---|---|
| 1,2,4-trimethyl cyclohexane | 100.0 | 100.0 | 100.0 |
| Isopropyl benzene | 100.0 | 100.0 | 100.0 |
| n-Propyl-benzene | 82.2 | 100.0 | 100.0 |
| 1-Methyl, 3-ethyl benzene | 68.2 | 97.8 | 97.1 |
| 1-Methyl, 4-ethyl benzene | 70.6 | 100.0 | 97.2 |
| 1,3,5-tri-methyl benzene | 30.8 | 22.8 | 34.4 |
| 1-Methyl, 2-ethyl benzene | 100.0 | 96.9 | 97.9 |
| 1,2,4-trimethyl benzene | 56.5 | 50.6 | 58.2 |
| 1,2,3-trimethyl benzene | 63.1 | 57.6 | 64.9 |

Table III shows a comparison of the percentage conversion of C$_{9+}$ components obtained using Catalysts A, B, and C at moderate severity reaction conditions (340° C. and 1.5 LHSV). Catalyst C again shows a higher percent conversion of individual C$_9$ components present in the feed than Catalysts A or B.

TABLE III

Percent conversion at 340° C. and 1.5 LHSV

| Moderate C$_{9+}$ % Conversion Components | Catalyst A | Catalyst B | Catalyst C |
|---|---|---|---|
| Isopropyl benzene | 100.0 | 100.0 | 100.0 |
| n-Propyl-benzene | 45.5 | 100.0 | 100.0 |
| 1-Methyl, 3-ethyl benzene | 47.6 | 69.7 | 78.9 |
| 1-Methyl, 4-ethyl benzene | 52.7 | 71.4 | 81.3 |
| 1,3,5-tri-methyl benzene | 12.9 | 25.7 | 21.8 |
| 1-Methyl, 2-ethyl benzene | 67.7 | 80.0 | 86.2 |
| 1,2,4-trimethyl benzene | 52.4 | 55.5 | 53.5 |
| 1,2,3-trimethyl benzene | 63.6 | 65.2 | 63.6 |

Tables IV, V, and VI show a comparison of the total C9 percent conversion data for all three catalysts at a range of temperatures reflecting moderate reaction conditions, namely, at 340° C., 360° C., and 380° C., respectively.

TABLE IV

Total C$_9$ conversion at 340° C. and 1.5 LHSV

| Catalyst Type | Reaction Temperature, ° C. | C$_9$ conversion, % | Xylenes Selectivity, % |
|---|---|---|---|
| Catalyst A | 340 | 51.4 | 35.0 |
| Catalyst B | 340 | 61.2 | 46.5 |
| Catalyst C | 340 | 63.0 | 50.9 |

From the data shown in Table IV, it is clear that Catalyst C provides the highest conversion of C$_9$ components present in the feed at moderate reaction conditions (340° C. and 1.5 LHSV). It is also clear that Catalyst C provides higher xylene selectivity at moderate reaction conditions.

TABLE V

Total C$_9$ conversion at 360° C. and 1.5 LHSV

| Catalyst Type | Reaction Temperature, ° C. | C$_9$ conversion, % | Xylenes Selectivity, % |
|---|---|---|---|
| Catalyst A | 360 | 57.4 | 37.6 |
| Catalyst B | 360 | 64.7 | 54.7 |
| Catalyst C | 360 | 69.6 | 55.0 |

From the data shown in Table V, it is clear that Catalyst C provides the highest conversion of C$_9$ components present in the feed at reaction conditions of 360° C. temperature and 1.5 LHSV. It is also clear that Catalyst C provides higher xylene selectivity at reaction conditions of 360° C. and 1.5 LHSV).

TABLE VI

Total C$_9$ conversion at 380° C. and 1.5 LHSV

| Catalyst Type | Reaction Temperature, ° C. | C$_9$ conversion, % | Xylenes Selectivity, % |
|---|---|---|---|
| Catalyst A | 380 | 60.7 | 39.9 |
| Catalyst B | 380 | 68.1 | 57.9 |
| Catalyst C | 380 | 71.9 | 57.4 |

From the data shown in Table VI, it is clear that Catalyst C provides the highest conversion of C$_9$ components present in the feed at reaction conditions of 380° C. temperature and 1.5 LHSV. It is also clear that Catalyst C provides comparable xylene selectivity at the reaction conditions of 380° C. and 1.5 LHSV.

Table VII provides data on the total C9 conversion obtained under high severity reaction conditions (400° C. and 1.5 LHSV).

TABLE VII

Total C₉ conversion at 400° C. and 1.5 LHSV

| Catalyst Type | Reaction Temperature, °C. | C₉ conversion, % | Xylenes Selectivity, % |
|---|---|---|---|
| Catalyst A | 400 | 62.2 | 44.7 |
| Catalyst B | 400 | 67.8 | 60.5 |
| Catalyst C | 400 | 72.3 | 58.9 |

From the data shown in Table VII, it is clear that Catalyst C provides the highest conversion of $C_9$ components present in the feed at high severity reaction conditions (400° C. temperature and 1.5 LHSV). It is also clear that Catalyst C provides comparable xylene selectivity at high severity reaction conditions of 400° C. and 1.5 LHSV.

Table VIII shows comparative data for the percentage amounts of $C_6$-$C_8$ aromatics obtained using Catalysts A, B, and C at high severity reaction conditions (400° C. and 1.5 LHSV).

TABLE VIII

Percent $C_6$-$C_8$ obtained at 400° C. and 1.5 LHSV

| High Selectivity Components | Catalyst A | Catalyst B | Catalyst C |
|---|---|---|---|
| Benzene | 1.3 | 2.4 | 3.9 |
| Toluene | 9.0 | 17.5 | 23.3 |
| Ethylbenzene | 2.3 | 0.4 | 0.3 |
| m-xylene | 15.5 | 21.8 | 24.0 |
| p-xylene | 4.3 | 8.0 | 7.1 |
| o-xylene | 6.5 | 9.0 | 9.2 |
| Total xylenes | 26.3 | 38.8 | 40.3 |

From the data shown in Table VIII, Catalyst C shows a higher percent amount of mixed xylenes obtained. Catalyst C also shows the highest amount of benzene and toluene and the lowest amount of ethylbenzene obtained by the three catalysts, making Catalyst C the catalyst of choice.

Table IX shows comparative data for the percentage amounts of $C_6$-$C_8$ aromatics obtained using Catalysts A, B, and C at moderate reaction condition severity (340° C. and 1.5 LHSV).

TABLE IX

Percent $C_6$-$C_8$ obtained at 340 C. and 1.5 LHSV

| Moderate Selectivity Components | Catalyst A | Catalyst B | Catalyst C |
|---|---|---|---|
| Benzene | 0.0 | 1.1 | 1.7 |
| Toluene | 5.1 | 10.0 | 13.6 |
| Ethylbenzene | 1.6 | 2.0 | 1.8 |
| m-xylene | 9.3 | 15.8 | 17.5 |
| p-xylene | 2.5 | 5.2 | 5.6 |
| o-xylene | 5.2 | 5.9 | 6.7 |
| Total xylenes | 17.0 | 26.9 | 29.8 |

From the data shown in Table IX, Catalyst C shows a higher percent amount of mixed xylenes obtained. Catalyst C also shows the highest amount among of benzene and toluene obtained, and an amount of ethylbenzene obtained that is comparable to Catalyst A and Catalyst B.

It is to be understood that the present invention is not limited to the embodiments described above, but encompasses any and all embodiments within the scope of the following claims.

We claim:

1. A method of converting C9+ alkylaromatic hydrocarbons to BTX (benzene-toluene-xylene), comprising the steps of:
   reducing a multiple zeolite catalyst with hydrogen gas at 400° C., the multiple zeolite catalyst consisting of:
   mordenite having a silica to alumina ratio of about 240 to 1;
   ZSM-5 having a silica to alumina ratio of about 30 to 1;
   alumina binder, the mordenite and the ZSM-5 forming a homogenous mixture with the binder; and
   molybdenum added to the mixture of the alumina binder, the mordenite, and the ZSM-5, the molybdenum forming about 3 wt. % of the catalyst;
   contacting a feed consisting essentially of C9+ alkylaromatic hydrocarbons with the reduced multiple zeolite catalyst and hydrogen in a transalkylation zone of a reactor at a pressure between 1.0 to 3.0 MPa, a temperature of 300° C. to 500° C., a space velocity of 1.0 to 5.0 $hr^{-1}$, and a hydrogen to hydrocarbon ratio of 1 to 4 to produce an effluent in a single-stage process;
   stripping C5 and lighter hydrocarbons and stripping unreacted feed from the effluent; and
   collecting BTX product from the effluent.

2. The method of converting C9+ alkylaromatic hydrocarbons to BTX according to claim 1, wherein the C9+ alkylaromatic hydrocarbon feed contains trimethylbenzenes and methylethylbenzenes in major amounts.

3. The method of converting C9+ alkylaromatic hydrocarbons to BTX according to claim 1, wherein the C9+ alkylaromatic hydrocarbon feed contains at least about 95 wt. % total aromatics.

4. The method of converting C9+ alkylaromatic hydrocarbons to BTX according to claim 1, wherein said step of contacting the feed comprises reacting the feed at a temperature between 330-450° C.

5. The method of converting C9+ alkylaromatic hydrocarbons to BTX according to claim 1, wherein said step of contacting the feed comprises reacting the feed at a liquid hourly space velocity of between 1-3 $hr^{-1}$.

6. The method of converting C9+ alkylaromatic hydrocarbons to BTX according to claim 1, wherein said reactor is a fixed bed reactor.

7. The method of converting C9+ alkylaromatic hydrocarbons to BTX according to claim 1, wherein said reactor is a moving bed reactor.

8. The method of converting C9+ alkylaromatic hydrocarbons to BTX according to claim 1, wherein said reactor is a radial-flow reactor.

* * * * *